United States Patent [19]

Weuste et al.

[11] Patent Number: 5,741,897
[45] Date of Patent: Apr. 21, 1998

[54] PROCESS FOR PREPARING AN N-SUBSTITUTED ALDONAMIDE

[75] Inventors: Burkhard Weuste, Gummersbach; Andrea Katharina Jansen, Eschweiler, both of Germany

[73] Assignee: Akzo Nobel nv, Arnhem, Netherlands

[21] Appl. No.: 656,735

[22] Filed: Jun. 3, 1996

[30] Foreign Application Priority Data

Jun. 15, 1995 [EP] European Pat. Off. ............ 95201587

[51] Int. Cl.$^6$ .............................. C07H 1/00; C07H 13/12
[52] U.S. Cl. .............. 536/18.5; 536/17.9; 536/18.7; 536/53; 536/124
[58] Field of Search .................. 536/17.9, 18.7, 536/124, 53, 18.5

[56] References Cited

U.S. PATENT DOCUMENTS

| | | | |
|---|---|---|---|
| 2,746,916 | 5/1956 | Magariello et al. | 204/79 |
| 2,752,334 | 6/1956 | Walton | 260/211 |
| 5,336,765 | 8/1994 | Van et al. | 536/18.5 |
| 5,386,018 | 1/1995 | Au et al. | 538/124 |
| 5,401,839 | 3/1995 | Van et al. | 536/18.7 |
| 5,403,922 | 4/1995 | Garelli-Calvet et al. | 536/1.11 |

FOREIGN PATENT DOCUMENTS

| | | | |
|---|---|---|---|
| 0 541 467 | 5/1993 | European Pat. Off. | C07C 235/10 |
| 0 550 106 | 7/1993 | European Pat. Off. | C07H 15/04 |
| 0 718 305 | 6/1996 | European Pat. Off. | C07H 15/04 |

*Primary Examiner*—John Kight
*Assistant Examiner*—Everett White
*Attorney, Agent, or Firm*—Ralph J. Mancini; Louis A. Morris

[57] ABSTRACT

The present invention generally relates to a process for preparing an N-substituted aldonamide by reacting an aldonic acid in a polar organic solvent with an amine of the formula $HNR^1(X-NR^1)nR^2$, wherein R1 and R~ may be the same or different and represent a hydrogen atom, a (cyclo)aliphatic or aromatic hydrocarbon separated by a hetero-atom or not, an amino acid ester, an amino acid amide, an ether amine or an N-alkanoyl alkylene diamine according to the formula $R^3-C(O)N(H)-R^4-$, wherein $R^3=C_1-C_{24}$ alkyl or alkenyl and $R^4=C_2-C_{22}$ branched or linear alkylene group, which may contain heteroatoms like N, O, and S, X is a difunctional (cyclo)aliphatic or aromatic hydrocarbon separated or not by a heteroatom or a hydrocarbon substituted hetero-atom, and n=0 or 1, with the proviso that when n=0, $R^1$ and $R^2$ do not stand for a hydrogen atom simultaneously, characterised in that an aqueous syrup of the aldonic acid is reacted, optionally after esterification with an alcohol with simultaneous distilling off of the water which is present, at a temperature in the range of 30° to 120° C., with the amine in the organic solvent, which is distilled off wholly or in part simultaneously with any water still present and/or formed.

16 Claims, No Drawings

PROCESS FOR PREPARING AN N-SUBSTITUED ALDONAMIDE

FIELD OF THE INVENTION

The invention pertains to a process for preparing an N-substituted aldonamide.

BACKGROUND OF THE INVENTION

Processes for preparing aldonamides have been described in detail in U.S. Pat. Nos. 2,752,334 and 5,336,765. The former patent discloses a process in which purified lactobionolactone is added to a slight excess of the amine in a solution of methanol or ethanol, followed by boiling with refluxing for ½ to 1½ hours, followed by hot filtration to remove the solid constituents. The solution is then allowed to cool, whereupon the N-substituted lactobionamide crystallizes. The latter patent discloses a process in which, after reaction of the lactone, more particularly aldobiono-1,5-lactone, with a primary or secondary amine, the reaction mixture is crystallized and filtered, and the filtrate is passed through an anionic exchange column. This results in the starting amine and the aldobionamide ending up in the eluate. The salt is retained in the column and then, after conversion via the acid into the lactone, reincorporated into the reaction mixture.

In actual practice, the known processes employing an aldonolactone as a starting product will give a yield of 70 to 90%. Aldonolactones are commercially available products, e.g., from Aldrich Chemicals. They can be prepared from a solution of an aldonic acid in an organic solvent such as dioxane or methanol. An alternative preparative process comprises spray-drying an aqueous solution of the corresponding acid which is disclosed in U.S. Pat. No. 2,746,916.

Aldonic acids are generally obtained, by fermentative, electrochemical or catalytic oxidation of the corresponding aldoses. Irrespective of the preparative process employed, the result in each case is a solution of an aldonic acid in water. Examples of suitable aldonic acids according to the invention include lactobionic acid, maltobionic acid or an acid mixture obtained from starch hydrolysis. Further, good results are obtained when use is made of an aqueous syrup of gluconic acid, galactonic acid or arabonic acid.

It will be evident that the known processes for preparing N-substituted aldonamides in which use is made of the corresponding aldonolactones are time-consuming and hence expensive. Furthermore, the commercially available aldonolactones and those obtained by spraydrying or treating with organic solvents usually contain small amounts of free aldonic acids. In consequence, there is great need for a preparative process which does not require first drying the acid and then converting it into the corresponding lactone.

The present invention provides processes satisfying the above-defined need.

SUMMARY OF THE INVENTION

The present invention generally relates invention to a process for preparing an N-substituted aldonamide by reacting an aldonic acid in a polar organic solvent with an amine of the formula $HNR^1(X-NR^1)nR^2$, wherein $R^1$ and $R^2$ may be the same or different and represent a hydrogen atom, a (cyclo)aliphatic or aromatic hydrocarbon separated by a hetero-atom or not, an amino acid ester or an ether amine, X is a difunctional (cyclo)aliphatic or aromatic hydrocarbon separated or not by a hetero-atom or a hydrocarbon substituted hetero-atom, and n=0 or 1, with the proviso that when n=0, $R^1$ and $R^2$ do not stand for a hydrogen atom simultaneously.

DETAILED DESCRIPTION OF THE INVENTION

The present invention generally relates invention to a process for preparing an N-substituted aldonamide by reacting an aldonic acid in a polar organic solvent with an amine of the formula $HNR^1(X-NR^1)nR^2$, wherein $R^1$ and $R^2$ may be the same or different and represent a hydrogen atom, a (cyclo)aliphatic or aromatic hydrocarbon separated by a hetero-atom or not, an amino acid ester or an ether amine, X is a difunctional (cyclo)aliphatic or aromatic hydrocarbon separated or not by a hetero-atom or a hydrocarbon substituted hetero-atom, and n=0 or 1, with the proviso that when n=0, $R^1$ and $R^2$ do not stand for a hydrogen atom simultaneously.

In the process, an aqueous syrup of the aldonic acid is reacted, optionally after having been esterified with an alcohol with simultaneous distilling off of the water which is present, at a temperature in the range of 30° to 120° C., with the amine in the organic solvent, which is distilled off wholly or in part simultaneously with any water still present and/or formed.

The thus prepared aldonamide may be further purified if so desired, by recrystallization from an organic solvent, preference being given to a process in which the organic solvent used for recrystallization is a solvent selected from the group of acetonitrile, dimethyl formamide, or an alcohol having 1 to 6 carbon atoms.

Preference is given to a process where the solvent used for the recrystallization is the same as that used when reacting the acid or the ester with the amine. Very good results are attained in this case when the organic solvent is methanol or forms an azeotrope with water. Optimum results are generally obtained with a process where the ratio of the molar equivalents of aldonic acid to those of amine is chosen between 1.2:1 and 1.0:1.

The aldonic acid can be reacted with the amine via direct conversion with simultaneous discharge of the formed water, e.g., by means of the organic solvent forming an azeotrope with the water. However, the preferred process is one in which the acid is first esterified with an alcohol which simultaneously acts as a solvent for the aldonic acid. The esterification preferably takes place in the presence of an acid as catalyst. Examples of suitable catalysts include sulphonic acids such as benzene sulphonic acid, methane sulphonic acid, and, especially, p-toluene sulphonic acid.

Favourable results were obtained by employing methanol, ethanol, propanol, isopropanol and/or 2-methoxy-ethanol for the esterification of the aldonic acid, with the lower alcohols, more particularly methanol, being preferred. For, said alcohol is a good solvent for the aldonic acid, is easily distilled off from the reaction mixture, and can then be re-used as a solvent in the reaction of the ester and the amine.

Suitable amines according to the invention for preparing the N-substituted aldonamides satisfy the formula $HNR^1(X-NR^1)nR^2$, wherein $R^1$ and $R^2$ may be the same or different and represent a hydrogen atom, a (cyclo)aliphatic or aromatic hydrocarbon separated by a heteroatom or not, an amino acid ester, an amino acid amide, an ether amine or an N-alkanoyl alkylene diamine according to the formula $R^3$—C(O)N(H)—$R^4$—, wherein $R^3$=$C_1$-$C_{24}$ alkyl or alkenyl and $R^4$=$C_1$-$C_{22}$ branched or linear alkylene group, which may contain heteroatoms like N, O, and S, X is a difunctional (cyclo)aliphatic or aromatic hydrocarbon separated or not by a hetero-atom or a hydrocarbon substituted hetero-atom, and n=0 or 1, with the proviso that when n=0, $R^1$ and $R^2$ do not stand for a hydrogen atom simultaneously.

Many of these amines are commercially available from Akzo Nobel Chemicals under the trade designation Armeen.

There is no critical upper limit regarding the number of carbon atoms for $R^1$ and $R^2$. Examples of suitable groups for $R^1$, $R^2$ or $R^3$ include methyl, ethyl, propyl, butyl, amyl, hexyl, heptyl, nonyl, decyl, undecyl, dodecyl, tridecyl, tetradecyl, pentadecyl, hexadecyl, heptadecyl, and octadecyl, as well as unsaturated groups such as undecenyl, oleyl, linoleyl, linolenyl, and heptenyl. In addition, use may be made of aromatic groups such as phenyl and naphthyl and of mixed aliphatic-aromatic groups such as benzyl and phenylethyl. As examples of cycloaliphatic groups may be mentioned cyclopentyl and cyclohexyl. Examples of suitable groups for $R^4$ include ethylene, trimethylene, tetramethylene, pentamethylene, hexamethylene, heptamethylene, octamethylene, nonamethylene, decamethylene, methyl ethylene, methyl propylene, methyl butylene, and ethylene oxy ethylene.

Very favourable results have been attained so far employing N-cocoyl ethylene diamine, N-tallowoyl ethylene diamine, N-palmitoyl ethylene diamine, coco-amine, tallow amine, palmityl amine, and H-tallow amine, especially when the aldonic acid in question is lactobionic acid. Favourable results can likewise be obtained using polyamines, such as a triamine of the formula $RN(CH_2CH_2CH_2NH_2)_2$, wherein R stands for a dodecyl or cocoyl group. The resulting non-ionic compound is readily soluble in water and possesses biocidal properties.

In general, the aldonic acid and amine combined make up about 20 to 70, preferably 25 to 40, wt. % of the reaction mixture. The remainder of the reaction mixture is made up of a mixture of solvent and water. These percentages are not critical and variations either way continue to be possible.

In the case of direct amidation of the aldonic acid suitable solvents tend to be polar organic solvents which are water-miscible and have a boiling point generally in the range of 75° to 140° C. or form an azeotrope with water in said temperature range, and preferably in the range of 80° to 120° C. Examples of suitable solvents include acetonitrile, and dimethyl formamide, although preference is given to monovalent alcohols, including etheralcohols, more particularly those forming an azeotrope with water, preferably at a temperature in the range of 90° to 100° C. So far, very good results have been attained using propanol, butanol, and their homologues. In this connection may be mentioned: 1-propanol, 2-propanol, 1-butanol, 2-butanol, 2-methyl-1-propanol, 2-methyl-2-propanol, 1-pentanol, 2-pentanol, 3-pentanol, 3-methyl-1butanol, 3-methyl-2-butanol, 2-methyl-2-butanol, ethylene glycol monomethyl ether, ethylene glycol monoethyl ether, ethylene glycol monopropyl ether, ethylene glycol monobutyl ether, and propylene glycol monomethyl ethers.

So far, optimum results have been attained using 1-butanol with a boiling point of 117° C., which forms an azeotrope with water at 93° C. The reaction is commonly carried out under atmospheric pressure, but of course it can also be performed at higher or lower pressures. After conversion, the resulting reaction mixture is diluted with one of the above solvents, followed by cooling and crystallization.

According to the indirect amidation process, the aldonic acid is first esterified with a lower primary alcohol, methanol being preferred. The esterification is carried out in the presence of an acid catalyst, such as p-toluene sulphonic acid, p-TSA, at a temperature in the range of 50° to 60° C. Then vacuum is applied and the remaining water is removed by distillation. The clear ester solution is then diluted with further alcohol, followed by the addition of the primary or secondary amine, which may lead to a white crystalline precipitate. Optionally, before addition of the amine the esterification catalyst may be neutralized by a preferably stoichiometric amount of sodium methoxide or an alkali hydroxide or carbonate such as potassium hydroxide, sodium hydroxide and/or potassium carbonate. After stirring the homogeneous or heterogeneous mixture for about 2 to 5 hours, preferably at a temperature in the range of 30° to 60° C., the reaction mixture is cooled to room temperature and filtered, or the solvent removed and the product dried. Use of said process gives a yield of almost 100% with an extremely good product quality.

The N-substituted aldonamides are environmentally friendly products having useful physical properties (e.g., surfactancy), rendering them suitable for many applications in personal care, dental, detergent, and cosmetic areas. Especially aldobionamides derived from dodecyl or coco-amine were found to possess biocidal properties.

The invention will be illustrated with reference to the following examples, which are not to be construed as being limiting in any manner whatsoever.

EXAMPLE I 73 g (0.363 mole) of coco-amine (=Armeer® C ex Akzo Nobel Chemicals) were dissolved in 650 ml of 1-butanol and heated to 65° C. To this mixture were added, at a pressure of 300 mbar and over a period of 15 minutes, 161.6 g of a syrup containing 80 wt. % of lactobionic acid (0.363 mole). The mixture was heated to 100° C., in the course of which distillation of the azeotropic mixture started. About 150 g were removed in this manner over a period of 2 hours. After partial supplementation with some 1-butanol the distillation process continued for a further 3 hours, with 440 g being isolated. The residue was diluted with butanol to a solids content of 10 wt. %. Upon cooling about 163 g of virtually pure lactobionococo-amide crystallised. The result of gaschromatographic analysis was as follows: amide content: 90.8 wt. %; carbohydrate and/or side-product thereof: 7.7 wt. %; fatty amine: 15 wt. %.

EXAMPLE II 20 ml of methanol were heated to 55° C., whereupon 40 g of a 73%-syrup (0.082 mole) of lactobionic acid were added together with 0.29 g of ptoluene sulphonic acid. A clear, yellow solution was obtained. A 500 mbar vacuum was applied, after which, over a period of 3 hours, 1000 ml of methanol were added and distilled off in such a way as to keep the volume in the reactor at a constant level of 60 ml throughout. The solution was then diluted by adding 123 ml of methanol and 15.51 g of liquid Armeen C (0.077 mole). After 2 hours of boiling with refluxing the solvent was evaporated and the product dried. Gaschromatographic analysis revealed an amide content of over 95% and a fatty amine percentage not exceeding 0.5 wt. %. The remaining material was composed of carbohydrate and/or side-product thereof.

EXAMPLE II 28.5 g (0.14 mole) of coco-amine (Armeen® C ex Akzo Nobel Chemicals) were dissolved in 640 g of 1-butanol containing 20 wt. % of water and heated to 65° C. To this mixture were added, at a pressure of 300 mbar and over a period of 10 minutes, 64 g of a syrup containing 80 wt. % of lactobionic acid (0.16 mole). The mixture was boiled with refluxing and water being isolated until, after 4 hours, the temperature of the vapour phase corresponded to that of 1-butanol (117° C.). The aqueous phase isolated in the process was 124 g, the butanol phase 228 g. Next, the mixture was again boiled with refluxing for 60 minutes. Finally, about 20 g of butanol were distilled off with the last remaining reaction water. The solids content of the product contained 87.1 wt. % of amide; 12.1 wt. % of carbohydrate and/or side-product thereof; 0.8 wt. % of fatty amine. The butanol containing phases could be reused in the next batch.

EXAMPLE IV 23 ml of methanol were heated to 55° C., followed by adding 40.00 g of a 85-% syrup (0.095 moles) of lactobionic acid and 0.34 g of p-TSA, and stirring for 60 minutes at 55° C. Then vacuum was applied and about 500 ml methanol were dosed and distilled off during 90 minutes in such a way that the reaction volume remained constant at a level of about 60 ml. The solution was then diluted with 146 ml of methanol and 18.05 g of molten coco-amine (0.090 mole Armeen® C) were added. The mixture was refluxed for another two hours, followed by evaporation of the solvent and drying of the product. Gaschromatographic analysis revealed an amide content of 93.3 wt. %; a fatty amine content of 0.9 wt. %; and 5.8 wt. % of carbohydrate and/or side-product thereof.

EXAMPLE V 21 ml of methanol were heated to 55° C., followed by adding 50 g of a 60-% syrup (0.168 moles) of gluconic acid and 0.30 g of p-TSA. The reaction mixture was stirred for 60 minutes at 55° C. Then vacuum of about 500 mbar was applied and 625 ml methanol were dosed and distilled off during 150 minutes in such a way that the reaction volume remained constant at a level of about 70 ml. The clear solution was diluted with 129 ml methanol, followed by adding 32.01 g (0.159 mole) of liquid Armeen® C, as a result of which a white crystalline precipitate was formed. The heterogeneous mixture was heated under reflux for 120 minutes, cooled to room temperature, and filtered. The filter cake was washed with ether and dried (51.8 g). According to GLC analysis, the product contained 98.7 wt. % of gluconamide, 0.8 wt. % of carbohydrate and/or side-product thereof, and about 0.5 wt. % of residual fatty amine.

EXAMPLE VI 22 ml of methanol were heated to 55° C., followed by adding 41.1 g of a 76.6-% syrup of lactobionic acid and 0.16 g p-TSA. The reaction mixture was stirred for 60 minutes at 55° C. Then vacuum of about 500 mbar was applied and 1030 ml of methanol were used to strip water within 150 minutes. The solution was diluted with 57 ml methanol, followed by adding 17.70 g (0.088 mole) of liquid Armeen® C. The mixture was then stirred for 120 minutes at 55° C., followed by evaporation of the solvent and drying of the product. According to GLC-analysis, the product contained 90.6 wt. % of lactobionamide, 8.6 wt. % of carbohydrate and/or side-product thereof, and 0.7 wt. % of residual fatty amine.

EXAMPLE VII 212.9 g of a 56.5% syrup of lactobionic acid (0.336 mole) were concentrated by distilling off 59.2 g of water at 55° C. under reduced pressure. The vacuum was broke, and 105 ml of methanol were added together with 1.1 g of p-toluene sulphonic acid. Vacuum was reapplied, and about 4000 ml of methanol were dosed and distilled off in such a way that the reaction volume remained constant at a level of about 260 ml. After dilution with 404 ml of methanol 1 g of sodium methoxide (30% solution in methanol) and 64.72 g of liquid Armeen® (0.321 mole) were added, and the mixture was stirred at 55° C. for about five hours, followed by evaporation of the solvent and drying of the product. Gas chromatographic analysis revealed an amide content of 93.4 wt. %, a fatty amine content of 0.7 wt. %, and 5.9 wt. % of carbohydrate and/or side-product thereof.

EXAMPLE VIII

The procedure described in Example VII was repeated, except that 50.49 g of decylamine (0.321 mole) were added and the mixture was stirred at 55° C. for three hours, followed by evaporation of the solvent and drying of the product. Gas chromatographic analysis revealed an amide content of 90.3 wt. %, a decylamine content of 1.1 wt. %, and 8.7 wt. % of carbohydrate or side-product thereof.

EXAMPLE IX 26 ml of methanol were heated to 55° C., after which 50 g of a 74.9% syrup of maltobionic acid (0.105 mole) and 0.37 g of p-TSA were added. The reaction mixture was stirred at 55° C. for 60 minutes. Next, vacuum was applied, and about 1000 ml of methanol were dosed and distilled off in such a way that the reaction volume remained constant at a level of about 80 ml. The solution was then diluted with 68 ml of methanol. After the addition of 21.10 g of Armeen® C (0.105 mole) the mixture was stirred at 55° C. for two hours, followed by evaporation of the solvent and drying of the product. Gas chromatographic analysis revealed an amide content of 93.6 wt. %, a fatty amine content of 1.7 wt. %, and 4.7 wt. % of carbohydrate or side-product thereof.

EXAMPLE X 39 ml of methanol were heated to 55° C., after which 74.1 g of a 76.6% syrup of lactobionic acid (0.159 mole) and 0.57 g of p-TSA were added. The reaction mixture was stirred at 55° C. for 60 minutes. Next, vacuum was applied, and about 1110 ml of methanol were dosed and distilled off in such a way that the reaction volume remained constant at a level of about 113 ml. The solution was then diluted with 103 ml of methanol, and 40.73 g of N-cocopropylene diamine (=Duomeen® C ex Akzo Nobel Chemicals) (0.159 mole) were added. The mixture was stirred at 55° C. for two hours, followed by evaporation of the solvent and drying of the product. According to analysis the product still contained about 6.3% of Duomeen® C, indicating a partial reaction of the secondary amine, resulting in a bisamide in addition to the desired aminoamide.

EXAMPLE XI 40 ml of methanol were heated to 55° C., after which 75.2 g of a 76.6% syrup of lactobionic acid (0.161 mole) and 0.58 g of p-TSA were added. The reaction mixture was stirred at 55° C. for 60 minutes. Next, vacuum was applied, and about 1130 ml of methanol were used to strip water. The remaining mixture (115 ml) was then diluted with 104 ml of methanol, and 24.99 g of N,N-bis-(3-aminopropyl) lauryl amine (0.080 mole) were added.

The mixture was stirred at 55° C. for two hours, followed by evaporation of the solvent and drying of the product, which did not contain any detectable amount of free amine.

EXAMPLE XII 212.9 g of a 56.5% syrup of lactobionic acid (0.336 mole) were concentrated by distilling off 59.2 g of water at 55° C. under reduced pressure. The vacuum was broken, and 105 ml of methanol were added together with 1.1 g of p-toluene sulphonic acid. Vacuum was reapplied, and about 4000 ml of methanol were dosed and distilled off in such a way that the reaction volume remained constant at a level of about 260 ml. After dilution with 404 ml of methanol 1 g of sodium methoxide (30% solution in methanol) and 86.10 g of tallow amine (=Armeen® T ex Akzo Nobel Chemicals) (0.321 mole) were added. The heterogeneous mixture was stirred at 55° C. for about five hours, followed by evaporation of the solvent and drying of the product. Gas chromatographic analysis revealed an amide content of 94.8 wt. %, a fatty amine content of 0.8 wt. %, and 4.4 wt. % of carbohydrate and/or side-product thereof.

We claim:

1. A process for preparing an N-substituted aldonamide by reacting an aldonic acid in a polar organic solvent with an amine of the formula $HNR^1(X-NR^1)nR^2$, wherein $R^1$ and $R^2$ may be the same or different and represent a hydrogen atom, a (cyclo)aliphatic or aromatic hydrocarbon separated by a hetero-atom or not, an amino acid ester, an amino acid amide, an ether amine or an N-alkanoyl alkylene diamine according to the formula $R^3-C(O)N(H)-R^4-$, wherein $R^3=C_1-C_{24}$ alkyl or alkenyl and $R^4=C_2-C_{22}$ branched or linear alkylene group, which may contain heteroatoms, X is a difunctional (cyclo)aliphatic or aromatic hydrocarbon separated or not by a hetero-atom or a hydrocarbon substituted hetero-atom, and n=0 or 1, with the proviso that when n=0, $R^1$ and $R^2$ do not stand for a hydrogen atom simultaneously, wherein an aqueous syrup of the aldonic acid is reacted, optionally after esterification with an alcohol with simultaneous distilling off of the water which is present, at a temperature in the range of 30° to 120° C., with the amine in the organic solvent, which is distilled off wholly or in part simultaneously with any water still present and/or formed.

2. The process of claim 1 wherein the prepared aldonamide is further purified by recrystallization from an organic solvent.

3. The process of claim 2 wherein the organic solvent employed in the recrystallization process is the same as that used in the reaction of the acid or the ester and the amine.

4. The process of claim 1 wherein the organic solvent employed is a solvent selected from the group of acetonitrile, dimethyl formamide, or an alcohol having 1 to 6 carbon atoms.

5. The process of claim 1 wherein the organic solvent forms an azeotrope with water.

6. The process of claim 1 wherein the organic solvent is methanol.

7. The process of claim 1 wherein for the esterification of the aldonic acid an alcohol is employed which simultaneously acts as a solvent for the aldonic acid.

8. The process of claim 1 wherein the esterification is carried out in the presence of an esterification catalyst.

9. The process of claim 8 wherein the esterification catalyst employed is p-toluene sulphonic acid.

10. The process of claim 1 wherein the alcohol employed in the esterification process is selected from the group consisting of methanol, ethanol, propanol, isopropanol, ethylene glycol monomethyl ether and mixtures thereof.

11. The process of claim 1 wherein in the case of direct amidation of the acid with the amine the reaction temperature is selected in the range of 80° to 120° C.

12. The process of claim 1 wherein in the case of indirect amidation of the acid with the amine the reaction temperature is selected in the range of 30° to 60° C.

13. The process of claim 1 wherein an aqueous syrup of lactobionic acid, maltobionic acid or an acid mixture obtained from starch hydrolysis is employed as the starting product for the aldonic acid.

14. The process of claim 1 wherein an aqueous syrup of gluconic acid, galactonic acid, glucoheptonic acid, arabonic acid, or mixtures thereof is employed as the starting product for the aldonic acid.

15. The process of claim 1 wherein said amine is selected from the group consisting of coco-amine, tallow amine, palmityl amine and H-tallow amine.

16. The process of claim 1 wherein said amine is selected from the group consisting of N-cocoyl ethylene diamine, N-palmitoyl ethylene diamine and N-tallowoyl ethylene diamine.

* * * * *